US008802171B2

(12) United States Patent
Watson

(10) Patent No.: US 8,802,171 B2
(45) Date of Patent: Aug. 12, 2014

(54) LIVE ORGANISM PRODUCT

(76) Inventor: James B. Watson, Pierce, NE (US)

( * ) Notice: Subject to any disclaimer, the term of this patent is extended or adjusted under 35 U.S.C. 154(b) by 804 days.

(21) Appl. No.: 12/287,181

(22) Filed: Oct. 7, 2008

(65) Prior Publication Data

US 2009/0074725 A1 Mar. 19, 2009

Related U.S. Application Data

(63) Continuation-in-part of application No. 11/055,433, filed on Feb. 10, 2005, now abandoned, which is a continuation-in-part of application No. 10/853,346, filed on May 25, 2004, now abandoned.

(51) Int. Cl.
| | | |
|---|---|---|
| A23L 1/28 | (2006.01) | |
| A01N 63/00 | (2006.01) | |
| C12N 1/00 | (2006.01) | |
| C12N 1/12 | (2006.01) | |
| A61K 39/02 | (2006.01) | |
| A23K 1/00 | (2006.01) | |
| A23L 1/30 | (2006.01) | |
| A61K 39/00 | (2006.01) | |

(52) U.S. Cl.
CPC ............ *A61K 39/02* (2013.01); *A23L 1/3006* (2013.01); *A23K 1/009* (2013.01); *A61K 2039/522* (2013.01); *A61K 2039/5254* (2013.01)
USPC .......... 426/61; 424/93.4; 435/243; 435/252.1

(58) Field of Classification Search
CPC ............ A61K 39/02; A61K 2039/522; A61K 2039/5254; A23K 1/009; A23L 1/3006
USPC .................. 426/61; 424/93.4; 435/243, 252.1
See application file for complete search history.

(56) References Cited

U.S. PATENT DOCUMENTS

| | | |
|---|---|---|
| 3,034,968 A | 5/1962 | Johnston et al. |
| 4,161,397 A | 7/1979 | Bellet et al. |
| 4,518,696 A | 5/1985 | Gehrman et al. |
| 4,810,494 A | 3/1989 | Welsh |
| 4,927,763 A | 5/1990 | Sudoma et al. |
| 5,624,684 A | 4/1997 | Fuisz |
| 5,725,853 A | 3/1998 | Dennis et al. |
| 6,443,369 B1 | 9/2002 | Dohrmann et al. |
| 2002/0119237 A1 | 8/2002 | Hevey |

FOREIGN PATENT DOCUMENTS

| | | |
|---|---|---|
| WO | WO 92/12234 | 7/1992 |
| WO | WO 92/12639 | 8/1992 |
| WO | WO 02/00035 | 1/2002 |
| WO | WO 03/053397 | 7/2003 |

OTHER PUBLICATIONS

Truong-Le et al., 2007, US 20070259334 A1.*
Elmore et al (2003, International Journal of Toxicology, 22, Supplement 1:37-102, "Final Report on the Safety Assessment of Aluminum Silicate, . . . ") abstract only).
Dennett, et al (2000, Journal of the American Mosquito Control Association; 16: 342-345, "Evaluation of Methylated Soy Oil and Water-Based Formulations of Bacillus . . . ").

* cited by examiner

*Primary Examiner* — Sin Lin Chen
(74) *Attorney, Agent, or Firm* — Advent, LLP

(57) ABSTRACT

A live organism product wherein the organisms are in a dormant state and are suspended in a liquid carrier which is sufficiently devoid of moisture so that the organisms will remain in a dormant state for several months. The carrier is comprised of oil. The carrier may also include an absorbent. The product is stored and shipped in a plastic bag and is sprayed onto its target host or the like. The moisture and pH then activates the organisms.

8 Claims, 3 Drawing Sheets

LIVE ORGANISM PRODUCT

CROSS-REFERENCE TO RELATED APPLICATION

This is a continuation-in-part application of the application Ser. No. 11/055,433 filed Feb. 10, 2005, now abandoned entitled LIVE ORGANISM PRODUCT, which is a continuation-in-part application of Petitioner's earlier application Ser. No. 10/853,346 filed May 25, 2004, now abandoned entitled "LIVE BACTERIA PRODUCT".

BACKGROUND OF THE INVENTION

1. Field of the Invention

This invention relates to a dormant organism product and more particularly to a live dormant organism product wherein live organisms, that are in a dormant state, are suspended in a clear liquid fluid carrier or medium that can be easily pumped and will stay in suspension for the life of the product. More particularly, the carrier, while being in a liquid state, is sufficiently devoid of moisture to prevent the organisms from becoming activated until the product is applied to feeds, forages, or directly onto animals such as livestock or the like. Hereinafter, feeds, forages, animals, livestock or the like will be referred to as "the target host".

2. Description of the Related Art

Live bacteria formulations are frequently applied to forage products, feed, etc., to enhance fermentation and/or digestion. The prior art products fall generally into two categories which are either a dry soluble powder form or a dry granular non-soluble form. The dry granular products are directly applied to its target host through a metering device such as a Gandy box, usually at a rate of 4 to 16 ounces per ton of forage treated. The dry soluble products must first be hydrated with water, then applied to its target host within a 48-hour time period post-hydration with application made through a liquid pump system at the rate of 37 grams to 1 gallon per ton of forage.

The dry granular products of the prior art, even if packaged in plastic pails, will sometimes come into direct contact with ambient air during manufacturing and processing or upon simply opening the product lid with the ambient air containing moisture or humidity. The moisture or humidity will activate the dormant bacteria upon contact which in turn causes the bacteria to inadvertently live and die before it can be applied to the forage. The value of the product will then be a total loss. The limestone carriers of the prior art products will carry minute traces of moisture, and such moisture severely reduces the product's ability to sustain an adequate shelf life. If the prior art product is a soluble powder product, it will also need to be hydrated before application. The hydration immediately activates all of the dormant bacteria and the producer has to apply the entire mixture within a 48-hour time frame or before since the bacteria will naturally deplete its food source and die, creating a total loss of the product value.

Further, the prior art products on the market today must be either removed from their original shipping container or physically poured into a dry applicator prior to application, or they must be contaminated with water, reducing their shelf life to less than 48 hours, post-contamination. Additionally, the prior art dry granular products have a tendency of sorting during shipment. This shakes any fines to the bottom of the shipping container leaving the either larger or lighter material to work its way to the top. Since the bacteria attach themselves to these particles, they may also migrate with these particles. Other dry soluble powder products may settle to the bottom of the applicator tank upon hydration. This will depend greatly on the product's rate of dilution. As application rates decrease to meet the producer's ongoing needs of hauling less product to the field, the manufacturers must in turn make their products more condensed to meet these needs. Such limits the solubility of the product.

The dry granular products of the prior art require a significant percentage of the product to be applied to the material which results in uniform coverage becoming difficult. Dry soluble powders mixed with water carriers have attempted to achieve low inclusion rates for some time. However, such products result in droplets which are very large in their molecular size and weight resulting in that there are actually few droplets being delivered per treatment, an example being one ton of forage treated with only ten large droplets so uniform coverage is poor.

One prior art reference is U.S. Pat. No. 4,161,397 issued Jul. 17, 1979 to Bellet et al. In the Bellet et al. composition, it appears that 99% of the bacteria die within one day and the other 1% of the bacteria die within 20 days. Further, in Bellet et al., the composition is applied to seeds which have fungicide thereon thereby making the treated seeds inappropriate for feeding to livestock or the like. As will be pointed out hereinafter, Applicant's product is sufficiently devoid of moisture so that substantially all the bacteria remain alive but in a dormant state for several months.

SUMMARY OF THE INVENTION

A live bacteria product is disclosed wherein the live bacteria are in a dormant state and are suspended in a clear liquid fluid carrier or medium that may easily be pumped and will stay in suspension for the life of the product. More particularly, the carrier or medium for the live bacteria is comprised of a substantially moisture-free liquid which is comprised of: (1) mineral oil and polymers other than the bacteria; or (2) a processed oil obtained from either animal, vegetable or petroleum origins. In some cases, the carrier will also have a hydrophilic molecular sieve adsorbent (moisture scavenger) included therein.

The product of this invention is preferably applied to the target host at a micro-treatment rate of 2 to 28 grams per ton of target host being treated. In some cases, more or less percentages may be utilized. The live bacteria, by being suspended in the substantially moisture-free carrier, will remain dormant for several months, at least 7 to 12 months, until coming into contact with the target host at which time the moisture in the target host will cause the bacteria to be activated. The product of this invention is packaged in controlled shipping vessels such as polyurethane bags that reduce the risk of moisture contamination of any kind. The product is sold and shipped directly to the producer who will then take the collapsible bag of product and hook it directly to an applicator which applies the product to the target host. The target host may be forage, feed or the like. In some cases, the product may be sprayed directly onto animals such as chicks who will ingest the product while grooming themselves. Although the product is ideally an improved live bacterial product, the product may be freeze-dried live dormant organisms that require ambient moisture to begin proliferation including, but not limited to, modified live bacterial and viral vaccines such as Parvo, Bovine Rhinotracheitis, Leptospira, BVD, IBR and P13 or modified and non-modified pathogens.

It is therefore a principal object of the invention to provide an improved live dormant organism product which requires ambient moisture to begin proliferation.

Yet another object of the invention is to provide a live dormant organism product wherein live organisms, that are in a dormant state, are suspended in a clear liquid fluid carrier or medium that can be easily pumped and will stay in suspension for the life of the product.

Still another object of the invention is to provide a live dormant organism product which is free of moisture to prevent the organism from becoming activated until the product is applied to the target host.

Still another object of the invention is to provide a live dormant organism product which may be applied to a target host at an extremely small rate.

Still another object of the invention is to provide a live dormant organism product wherein the carrier or medium therefore is comprised of a substantially moisture-free liquid comprised of: (1) mineral oil and polymers other than the bacteria; or (2) a processed oil obtained from either animal, vegetable or petroleum origins.

Still another object of the invention is to provide a live dormant organism product which will not be activated until coming into contact with moisture associated with the target host.

Yet another object of the invention is to provide a live dormant organism product which may be applied to forage or feed at a preferred micro-treatment rate.

A further object of the invention is to provide a live dormant organism product which is packaged in such a way to limit its exposure to possible contamination from outside sources, such as moisture-laden air or fluid water of any kind.

Still another object of the invention is to provide a live dormant organism product such as modified or non-modified live bacterial and viral vaccines.

Still another object of the invention is to provide a live dormant organism product which will remain alive but dormant for several months, i.e., seven to twelve months.

These and other objects will be apparent to those skilled in the art.

DETAILED DESCRIPTION OF THE INVENTION

Figure 1:
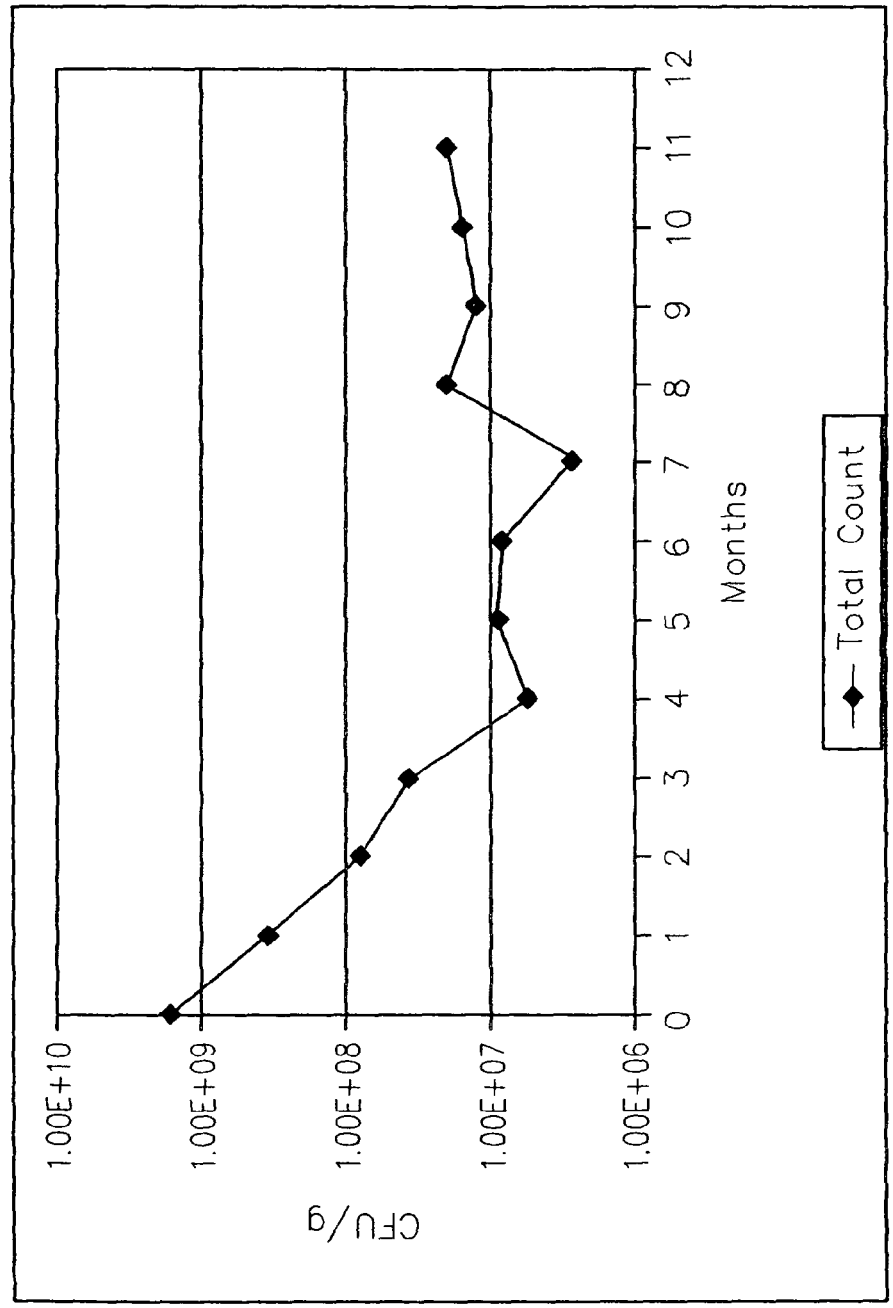
FIG. 1 is a graph referred to as Graph A.

In the following, the product of this invention is described as a live dormant bacteria product. However, it should be understood that the product could be: (1) a live dormant organism requiring ambient moisture to begin proliferation; (2) modified or live bacterial and viral vaccines such as Parvo, Bovine Rhinotracheitis, Leptospira, BVD, IBR and P13; or (3) modified and non-modified pathogens.

In this invention, conventional live viable harmless bacteria are mixed with a substantially moisture-free liquid carrier or medium. In general, the live bacteria used in the product of this invention will be any lactic acid producing bacteria that is permissible for use in animal related products. The United States Food and Drug Administration (FDA) and The American Association of Feed Control Officials (AAFCO) have published a list of the microorganism species which are "generally recognized as safe" (GRAS) for use in direct-fed microbial products. Table I hereinbelow lists presently approved bacteria for use with animal related products.

TABLE I 36.14--DFM Microorganisms under the "GRAS" Status

*Aspergillus niger*
*Aspergillus oryzae*
*Bacillus coagulans*
*Bacillus lentus*
*Bacillus licheniformis*
*Bacillus pumilus*
*Bacillus subtilis*
*Bacteroides amylophilus*
*Bacteroides capillosus*
*Bacteroides ruminocola*
*Bacteroides suis*
*Bifidobacterium adolescentis*
*Bifidobacterium animalis*
*Bifidobacterium bifidum*
*Bifidobacterium infantis*
*Bifidobacterium longum*
*Bifidobacterium thermophilum*
*Lactobacillus acidolphilus*
*Lactobacillus brevis*
*Lactobacillus buchneri*
*Lactobacillus bulgaricus*
*Lactobacillus casei*
*Lactobacillus curvatus*
*Lactobacillus delbruekii*
*Lactobacillus fermentum*
*Lactobacillus helveticus*
*Lactobacillus lactis*
*Lactobacillus plantarum*
*Lactobacillus euterii*
*Leuconostoc mesenteroides*
*Pediococcus acidilacticii*
*Pediococcus cervisiae*
*Pediococcus pentosaceus*
*Propionibacterium freudenreichii*
*Propionibacterium shermanii*
*Saccharomyces cerevisiae*
*Entercococcus cremoris*
*Entercococcus diacetylactis*
*Entercococcus faecium*
*Entercococcus intermedius*
*Entercococcus lactis*
*Entercococcus thermophilius*
*Lactobacillus cellobiosus*

Preferably, the moisture-free liquid carrier is comprised of a product marketed under the trademark "SYNERGEL®" manufactured by Penreco of 138 Petrolia Street, Karns City, Pa. 16041-9799. The product is generally referred to as a gelled mineral oil, reference number 1004-100, having a Brookfield viscosity of 1242 cPs. The carrier product is clear, odorless and is insoluble in water. The carrier also includes polymers. Other suspension agents such as COBISAL™ (polymer fiber) may also be used from time to time to aid or reduce the possibility of the settling of the bacteria therein. While the moisture-free oil described above is preferred, a processed oil obtained from either animal, vegetable or petroleum may be used. The product of this invention is designed to only activate the bacteria at the physical point of contact with the target host. Upon contact, the target host ambient moisture content will activate the dormant bacteria found within the liquid microbial medium or carrier. The liquid microbial medium or carrier of this invention has undergone a special production process developed by Penreco. The process consists of first passing the mineral oil through an advanced filtration system which specifically targets and absorbs any ambient moisture. Secondly, the mineral oil is heated and polymers are added to increase the oil viscosity and suspension qualities. Thirdly, the oil is packaged into controlled shipping vessels that reduce the risk of moisture contamination of any kind.

Upon receipt of the packaged carrier, applicant then preferably adds a moisture scavenger product such as a hydrophilic molecular sieve adsorbent as an insurance program. The adsorbent may comprise a natural or synthetic zeolite consisting of crystalline metal aluminosilicate, alkali metal aluminosilicate or sodium aluminosilicate. Finally, whatever bacteria are needed for a particular purpose will then be added. The final blend is then packaged in moisture and ultraviolet retardant containers such as collapsible polyurethane bags, very similar to I.V. bags. The product is then sold and shipped directly to the retailer and/or end user. The end user will then take the collapsible bag of liquid microbial blend and hook it directly to an applicator so that extremely small droplets are created which are sprayed upon the target host.

The invention described herein provides the ability to inoculate other products with dormant live bacteria, by means of a light spraying application. Whereas the bacteria is protected with the oil/polymer blend allowing the host bacteria to survive longer in a non-favorable environment, the coating of the bacteria cell walls with the oil/polymer covering provides a physical chemical moisture barrier. The above provides the ability to permit the live bacteria to be introduced onto a pelleted feed without immediately inadvertently activating the oil/polymer/host bacteria through ambient moisture contamination from the feed itself.

The product of this invention permits it to be applied to its target host at a preferred micro-treatment rate of 2 to 28 grams per one ton of forage or the material treated (with no additional water or carriers needed). In some cases, higher or lower ratios may be employed. Such micro-treatment is substantially less than prior art products that have treatment rates that range from 37.88 grams to 8.3453 pounds per one ton of forage treated.

The product of this invention and its packaging limits its exposure to possible contamination from outside sources, such as moisture-laden air or fluid water of any kind. The product of this invention is designed to only activate at the physical point of contact with the target host. Upon contact with the target host, the change in pH and moisture activates the dormant bacteria.

To remain 100% alive, freeze-dried bacteria must be kept free of water activity, kept out of direct ultra violet light, and maintained in temperatures less than 110° F. The best place to meet all of these criteria is to keep the bacteria in liquid nitrogen or a freezer. If kept frozen, the bacteria will remain alive and viable for many years. Unfortunately, if you want to apply these bacteria to agricultural needs, the bacteria must be taken out of the freezer and put into other types of carriers. In doing so, the bacteria are inadvertently exposed to ambient water activity.

Manufacturers have used oils for their residual effect and as a carrier for the freeze-dried bacteria under the assumption that oil would protect the bacteria from ambient moistures, thereby extending the life span of the bacteria. However, when the bacteria are placed in a feed grade mineral oil, the bacteria quickly die off in about 30 days. Another noted problem is that the bacteria in oil-based carriers quickly settle out, since the bacteria are non-soluble in oil.

In developing the product described in this application, Applicant realized the problems with putting freeze-dried bacteria in an oil-based carrier. Testing showed that the bacteria in a feed grade mineral oil had a very short life span as seen in FIG. 1. In FIG. 1, a one-log die off represents a 90% die off of live bacteria. For example, (1.00 E 09-to-1.00 E 08)=a 90% loss of live bacteria. A two-log loss, for example, (1.00 E 09-to-1.00 E07)=a 99% loss of live bacteria. A three-log loss represents a 99.9% loss of live bacteria and so on.

FIG. 1 demonstrates the life span of freeze-dried *Lactobacillus acidophilus* bacteria blended into a feed grade mineral oil. Please note that there was a 78.92% die off of the La bacteria in the first month, a 95.07% die off on the second month and a 97.78% total cumulative die off of the La bacteria upon the third month with a 99.67% die off on the fourth month.

Figure 2:
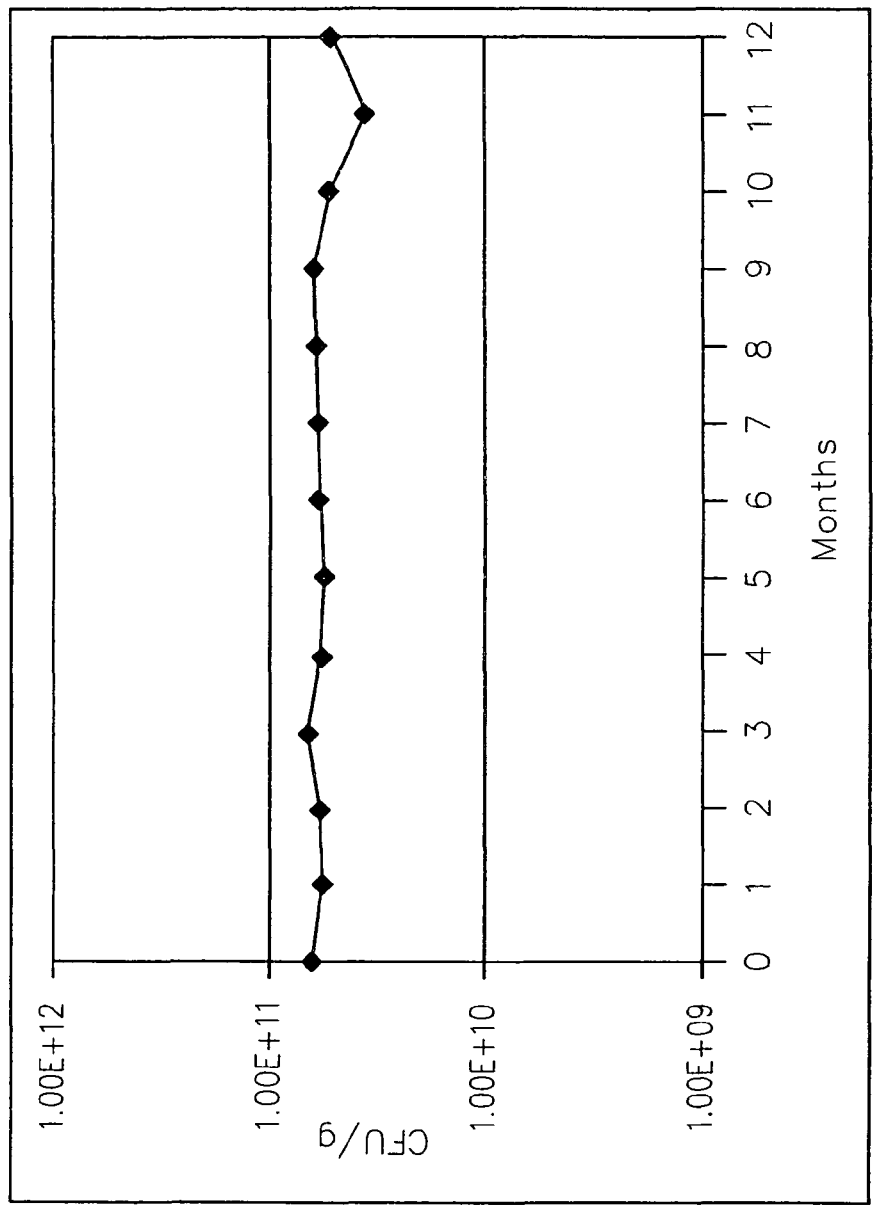
FIG. 2 is a graph referred to as Graph B.

FIG. 2 illustrates a test of *Lactobacillus acidophilus* bacteria blended into the carrier product described and claimed in this application and it can be seen that the bacteria in FIG. 2 lived for at least 12 months time, at which time the test was discontinued.

Figure 3:
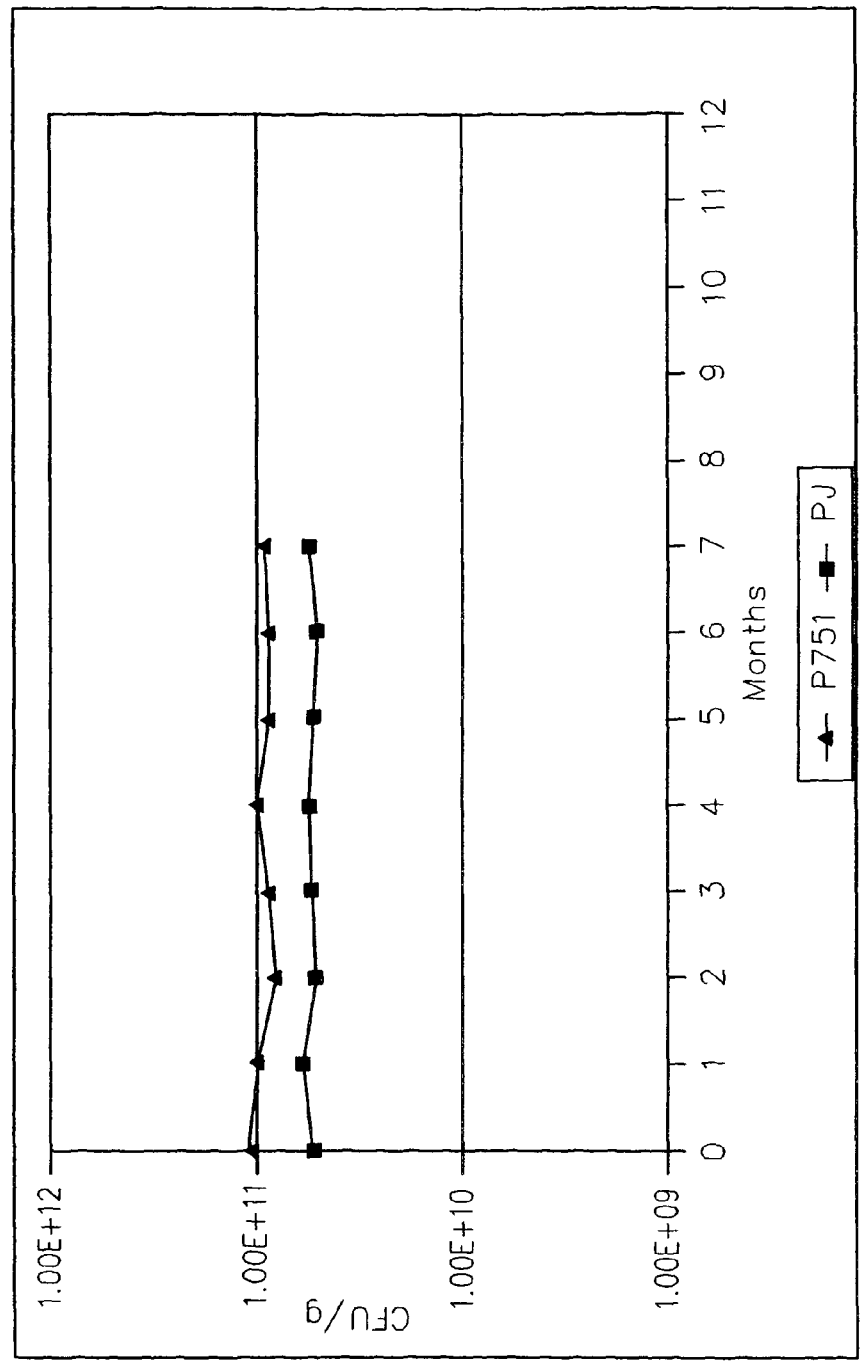
FIG. 3 is a graph referred to as Graph C.

FIG. 3 is a currently ongoing experiment, scheduled for 12 months testing. In its seventh month of testing, FIG. 3 shows two bacteria being separately tested in the product described and claimed in this application. In the tests of FIG. 3, (P751) *Pediococcus acidilaticii* and (PJ) *Pediococcus pentosaceus* were still 100% alive at 7 months time.

It can be seen from FIGS. 2 and 3, wherein the carrier of this application was utilized, the life span of the freeze-dried bacteria is greatly extended than that previously possible.

Thus it can be seen that the invention accomplishes at least all of its stated objectives.

The invention claimed is:

1. A method of forming a stabilized admixture, comprising the steps of:
   providing dormant viable bacteria;
   providing a liquid carrier which lacks sufficient moisture to hydrate dormant viable bacteria when the dormant viable bacteria are mixed therewith;
   heating the liquid carrier;
   providing a suspension agent;
   increasing the viscosity and suspension qualities of the liquid carrier by adding the suspension agent to the heated liquid carrier;
   forming a moisture barrier on the cells of the dormant viable bacteria by mixing the dormant viable bacteria into the liquid carrier and suspension agent admixture; and
   preventing the hydration of the dormant viable bacteria in the admixture for at least 7 to 12 months by placing the admixture into a moisture and ultraviolet retardant container.

2. The method of claim 1 wherein the liquid carrier is selected from the group consisting of a mineral oil, an oil obtained from animal origins, an oil obtained from vegetable origins, and an oil obtained from petroleum origins.

3. The method of claim 1 wherein said admixture includes a hydrophilic molecular sieve adsorbent.

4. The method of claim 3 wherein said adsorbent comprises a natural or synthetic zeolite.

5. The method of claim 4 wherein said zeolite comprises crystalline metal aluminosilicate.

6. The method of claim 4 wherein said zeolite comprises alkali metal aluminosilicate.

7. A method of forming a stabilized admixture, comprising the steps of:
   providing live, dormant bacterial vaccine;
   providing a liquid carrier which lacks sufficient moisture to hydrate live, dormant bacterial vaccine when the vaccine is mixed therewith;
   heating the liquid carrier;
   providing a suspension agent;
   increasing the viscosity and suspension qualities of the liquid carrier by adding the suspension agent to the heated liquid carrier; and forming a moisture barrier on the cells of the vaccine by mixing the vaccine into the liquid carrier and suspension agent admixture so that the vaccine will not hydrate for at least 7 to 12 months or until applied to a target host.

8. A method of forming a stabilized admixture, comprising the steps of:

providing live, dormant viral vaccine;

providing a liquid carrier which lacks sufficient moisture to hydrate live, dormant viral vaccine when the live, dormant, viral vaccine is subsequently mixed with the liquid carrier;

heating the liquid carrier;

providing a suspension agent;

increasing the viscosity and suspension qualities of the liquid carrier by adding the suspension agent to the heated liquid carrier; and forming a moisture barrier on the live, dormant, viral vaccine by mixing the live, dormant, viral vaccine into the liquid carrier and suspension agent admixture so that the live, dormant, viral vaccine will not hydrate for at least 7 to 12 months or until applied to a target host.

* * * * *